United States Patent

Abramson

[11] Patent Number: 5,620,424
[45] Date of Patent: Apr. 15, 1997

[54] DEVICE FOR PREVENTING CATHETER RELATED INFECTION

[76] Inventor: Daniel J. Abramson, 7671 San Mateo Dr. East, Boca Raton, Fla. 33433

[21] Appl. No.: 494,536

[22] Filed: Jun. 26, 1995

[51] Int. Cl.⁶ .................................................. A61M 5/32
[52] U.S. Cl. .................................. 604/265; 604/174
[58] Field of Search ........................... 604/174, 162, 604/163, 171, 181, 199, 265, 280, 178, 349, 356, 172, 52; 206/364, 365, 366, 367, 368, 369, 370; 128/767

[56] References Cited

U.S. PATENT DOCUMENTS

| | | | |
|---|---|---|---|
| 3,961,622 | 6/1976 | Edwards | 128/2 F |
| 4,080,970 | 3/1978 | Miller | 604/174 |
| 4,784,647 | 11/1988 | Gross | 604/265 |
| 4,834,711 | 5/1989 | Greenfield et al. | |
| 5,195,998 | 3/1993 | Abraham et al. | 604/351 |
| 5,236,422 | 8/1993 | Eplett, Jr. | 604/265 |
| 5,267,968 | 12/1993 | Russo | 604/174 |
| 5,334,166 | 8/1994 | Palestrant | 604/265 |
| 5,364,367 | 11/1994 | Banks et al. | 604/174 |
| 5,368,575 | 11/1994 | Chang | 604/174 |
| 5,484,420 | 1/1996 | Russo | 604/178 |

FOREIGN PATENT DOCUMENTS 0148560  8/1985  Japan .................................. 604/174

*Primary Examiner*—Vincent Millin
*Assistant Examiner*—Cris L. Rodriguez
*Attorney, Agent, or Firm*—Malin, Haley, DiMaggio & Crosby, PA

[57] ABSTRACT

An attachable device, for use with a catheter, and impregnated with, or containing, a supply of antiseptic solution, gel or powder, such that the device can be exteriorly positioned adjacent a catheter insertion site thereby dispensing antiseptic solution at the catheterization site for preventing microorganisms surrounding the insertion site from causing infection.

11 Claims, 4 Drawing Sheets

DEVICE FOR PREVENTING CATHETER RELATED INFECTION

BACKGROUND OF THE INVENTION

1. Field of the Invention

The present invention relates to devices for medical catheters for minimizing or preventing catheter related infection, and more particularly to a slidable and attachable catheter device that can be impregnated with silver ion, and/or contain and disperse an antiseptic substance such as silver sulfadiazine, or other suitable substance, for substantially reducing the incidence of catheter-related infection caused by colonization of bacteria or fungi around the point of catheter insertion with probable entry in to the tissues, or blood stream, at the catheter insertion site.

2. Description of the Background Art

The use of urethral catheters for draining bodily fluids and irrigation is well known in the art. It has been found that the rate of bacterial infection, associated with urethral catheterization, rises sharply in patients requiring prolonged catheter insertion, as is often necessary. Similar infection complications are also experienced with percutaneously inserted catheters and I.V. tubes. Likewise, the use of fluid drains for draining infectious or non-infectious fluids, or for blood or serum collection result in similar bacterial infection problems.

While it is possible for infectious bacteria to invade the body through catheter tubing lumen channels, a strong correlation has been shown between organisms colonizing skin at the insertion site and microorganisms causing catheter-related infection. It has been found that organisms penetrate from the site of catheter insertion around the outside of the catheter lumen into deeper tissues, or, in the case of venous catheters, directly into the blood stream. As a result, physicians routinely suppress the microorganism population around the catheter insertion site with an effective antiseptic prior to catheterization. However, it has been found that certain suppressed microorganisms grow back at a rapid rate leading to infection originating at the catheterization site.

With urethral catheters bacterial infection may occur in association with single or multiple catheterizations. With retention catheters bacterial infections rise precipitously, and it has been found that approximately 98 percent of patients experience bacterial infection within four days. Kass, E. H. and Sossen: *A Report on the Prevention of Infection of the Urinary Tract in the Presence of Indwelling Catheters*, Journal of the American Medical Association; 169:1181, 1959. With closed drainage systems, in which there is no manipulation, handling, or irrigation through the catheter lumens, infections have been found to occur later—within approximately ten days. These infections can lead to infections of the bladder, renal inflammation, ascending infection of the kidneys, and septicemia. Accordingly, studies have shown that infections can arise through the catheter lumen or from outside the catheter in the space between the catheter wall and the urethra. Kass, E. H. and Schneiderman, L. J., *Entry of Bacteria into the Urinary Tract of Patients with indwelling Catheters*, New England Journal of Medicine; 256:556, 1957. Since urethral secretions provide an excellent culture medium for bacterial growth, the inventor herein, has devised a catheter that allows for retrograde irrigation with antiseptic solutions to control infections. See Abramson, D. J., *A New Catheter Designed for Bladder Drainage and Urethral Irrigation*; Amer. Surgeon, 34:436, 1968.

In addition, percutaneously inserted central venous catheters are widely used for food, fluid and drug therapy, as well as for monitoring, and, not surprisingly, catheter-related bacteremia or fungemia is the most frequent serious complication associated with such use. When catheter tubes are inserted directly into large blood vessels, septicemia or fungemia results in 3–7 percent of cases. Several devices are known in the background art for preventing catheter-related infection associated with surgically implanted central venous catheters. One such device incorporates a cuff that creates a mechanical barrier against infection by skin organisms. Such a device is disclosed by Dennis G. Maki et al, *An Attachable Silver-Impregnated Cuff for Prevention of Infection with Central Venous Catheters: A Prospective Randomized Multicenter Trial*, The American Journal of Medicine 85:307, (September) 1988. The device studied by Maki consists of an attachable cuff made of biodegradable collagen to which silver ion is cheleated. With the prior art device, the cuff is attached to a catheter immediately prior to insertion, and positioned approximately 0.25 to 0.75 centimeters below the surface of the skin upon catheter insertion. Inserting the prior art cuff below the surface of the skin, however, can cause irritation and require an enlargement of the insertion site than would otherwise be required. However, even with the prior art cuff, catheter infection with organisms or fungi from the catheter insertion site did occur as approximately 20 percent of the catheters in control groups showed one or more signs of inflammation at the insertion site. In addition, the prior art cuff experienced the undesirable tendency to extrude extracutaneously, either partially or totally.

Likewise, the use of surgical drain to convey infected material from body cavities, or, as is often the case, to drain non-infectious collections of bodily fluids that accumulate before or after surgery, experience similar problems resulting from bacteria or fungi colonizing the site of drain insertion.

Therefore, a need exists for a bacterial barrier for a catheter that can be attached to a conventional catheter and exteriorly positioned adjacent the catheter insertion site for preventing micro-organisms surrounding the insertion site from causing infection.

SUMMARY OF THE INVENTION

The present invention is directed to an attachable device for use with urinary or central venous catheters, or surgical drains. The device may be fabricated from silicone rubber or other suitable material and may be impregnated with the silver ion, and/or contain a supply of antiseptic solution, gel, or powder for dispersal at the site of catheter insertion. The device is capable of being exteriorly positioned adjacent a catheter insertion site for preventing micro-organisms surrounding the insertion site from infecting the tissue surrounding an inserted catheter.

It is a principle object of the present invention to provide a bacterial barrier for preventing or decreasing the incidence of infection associated with catheterization.

Another object of the present invention is to provide a bacterial barrier, for preventing or decreasing the incidence of infection associated with catheter use, that is exteriorly positionable adjacent the catheter insertion site.

A further object of the present invention is to provide a bacterial barrier for preventing or decreasing the incidence of infection associated with catheter insertion that can be used with a wide variety of catheters.

Still another object of the present invention is to provide an attachable bacterial barrier for use with a catheter that contains a supply of antimicrobial or antiseptic ointment for preventing or decreasing the incidence of infection originating at a catheter insertion site.

Yet another object of the present invention is to provide a bacterial barrier for use with a catheter that can be replenished with antiseptic ointment or solution as needed.

In accordance with these and other objects which will become apparent hereinafter, the instant invention will now be described with particular reference to the accompanying drawings.

DESCRIPTION OF THE PREFERRED EMBODIMENTS

Figure 1:
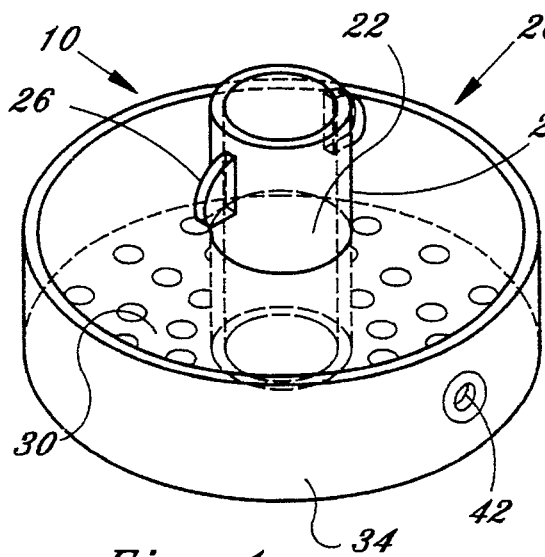
FIG. 1 is a perspective view of the catheter accessory device of the present invention.
Figure 2A:
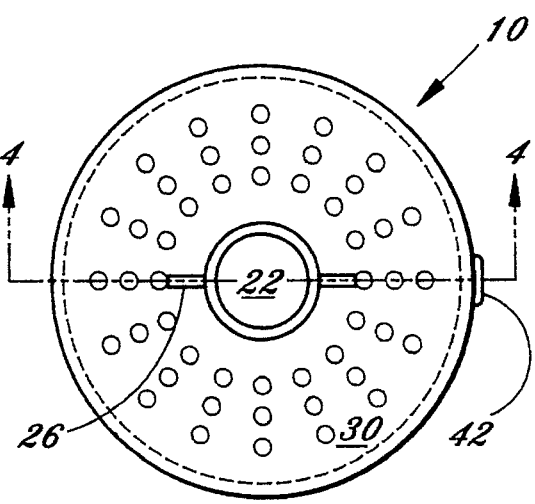
FIG. 2a is a top view of the catheter accessory device of the present invention.
Figure 2B:
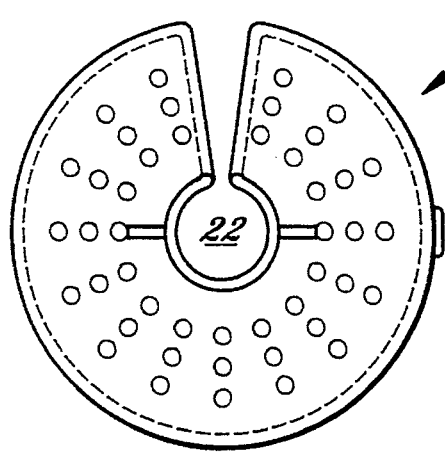
FIG. 2b is a top view of the C-shaped embodiment of the present invention.

With reference to FIGS. 1 through 9 there is depicted the catheter accessory device for preventing catheter related infection generally designated as 10. In a preferred embodiment the device includes a substantially disk-shaped body 20 having a centrally disposed aperture 22, defined by a catheter sleeve 24, for accommodating a catheter inserted therethrough. Body 20 and sleeve 24 may be fabricated of silicone, or any suitable material. Furthermore, body 20 may be C-shaped, as depicted in FIG. 2b generally as 10b, or O-shaped and having a slit extending through a portion of body 20 thereby bisecting the sleeve wall and enabling the device to be clipped, either on or off, to an inserted catheter without requiring catheter removal. The device is designed for use with a catheter for dispensing antiseptic solution proximal a catheter insertion site as best seen in section in FIGS. 3 and 6, by means that will soon become apparent.

Sleeve 24 further includes a means for grasping the device 10, such as a pair of extending tabs 26. Tabs 26 may be utilized for sliding body 20 along a catheter inserted therethrough for proper positioning adjacent the catheter insertion site. Tabs 26 may also be used for anchoring body 20 adjacent the catheterization site with surgical sutures.

Body 20 includes a top surface 30, a bottom surface 32, and an outer sidewall 34. Surfaces 30 and 32, sidewall 34 and sleeve 24, cooperate to form an enclosed space or reservoir 38 for containing a supply of antiseptic or antibiotic therein. Said antiseptic or antibiotic may comprise any one of the following forms: a solution; gel; powder; or any other suitable form (hereinafter "antiseptic solution").

Bottom surface 32 incorporates means for dispensing antiseptic solution at the point of catheter insertion. In a first embodiment, bottom surface 32 includes a plurality of apertures 40 for dispensing antiseptic solution from reservoir 38, to provide a source of medication at the point of catheter insertion into the body. In this embodiment, reservoir 38 may be pre-filled with antiseptic solution during the manufacturing phase, or it may be filled, and refilled in the field by a medical technician.

A sealing material or wrapper (not shown) may be attached to, or serve as packaging for, the device to maintain sterility and particularly for maintaining the sterility of bottom surface 32 during pre-use periods; the sealing material may be removed when use is required, thereby exposing apertures 40 and allowing for dispensing of antiseptic solution.

Body 20 may further incorporate means for filling reservoir 38 with antiseptic or antibiotic solution, either as an initial charge with a selected solution, or as a refill when the supply of solution is in need of replenishment or change. In the preferred embodiment a filling port 42 comprises a structure, such as a diaphragm, suitable for syringe 60 insertion for filling reservoir 38. In this embodiment a supply of solution is delivered to reservoir 38 by inserting a hypodermic needle through outer wall 34, via port 42, and injecting the desired solution. Port 42 may also comprise a self sealing luer lock which is known in the medical art as a suitable structure designed for use with a syringe hub (without an attached needle) to self-seal, or automatically return to a normally closed position, thereby preventing solution leakage, when the filling process is complete.

Figure 5:
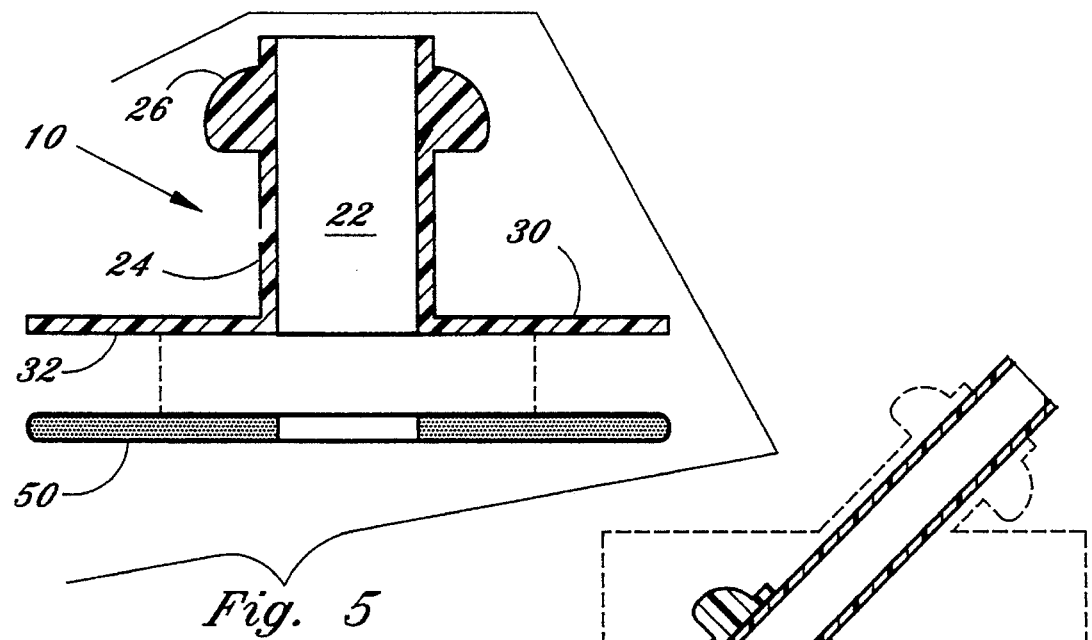
FIG. 5 is a sectional view of a first alternate embodiment of the catheter accessory device of the present invention.

In a second embodiment, depicted in FIG. 5, an antiseptic impregnated patch 50, of material such as gauze or a wick impregnated with an antiseptic such as silver sulfadiazine, is fixed to bottom surface 32 for providing a source of medication at the catheterization site. In addition, patch 50 may be used as the sole source of antiseptic, without reservoir 38 and solution dispensing apertures 40 of the first embodiment. When used as the sole source of antiseptic solution, patch 50 may incorporate an adhesive backing for removable attachment to bottom surface 32 such that patch 50 may be replaced periodically. In addition, patch 50 may be used in conjunction with dispensing apertures 40 for providing uniform dispersal of antiseptic or antibiotic solution.

Figure 3:
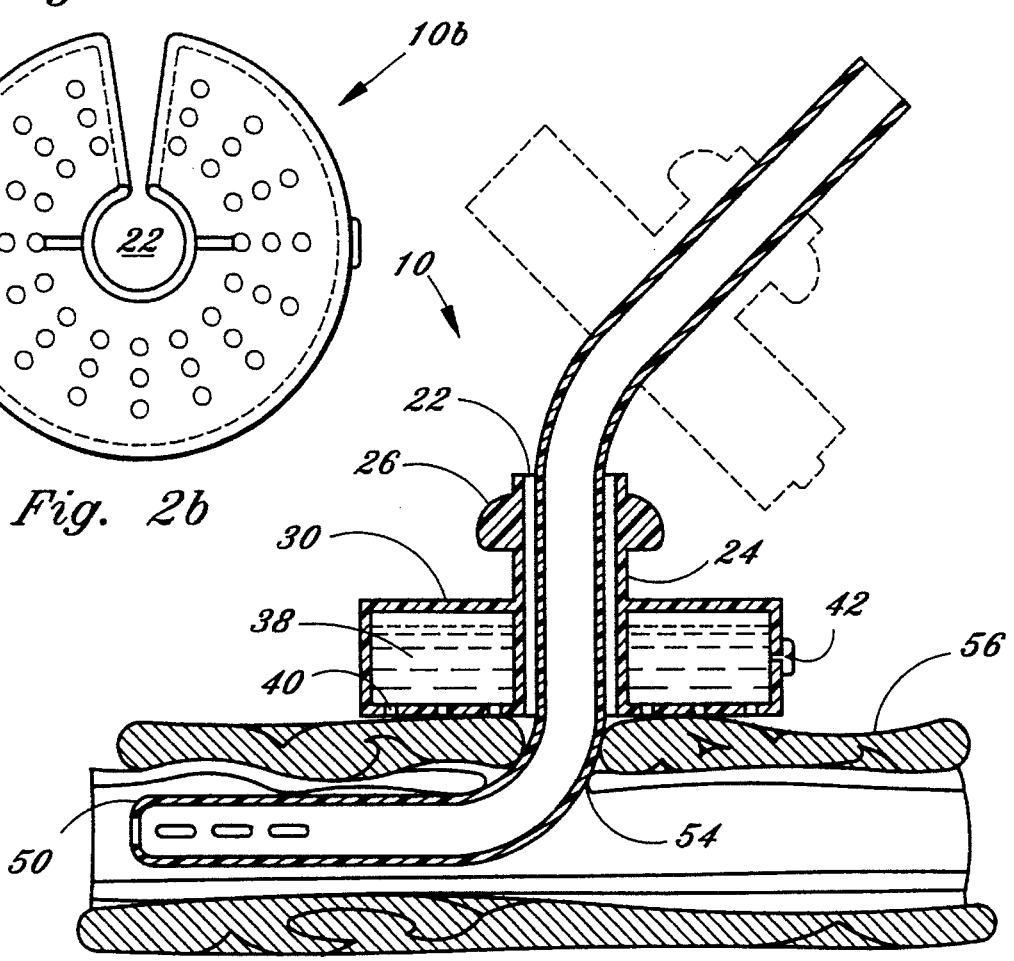
FIG. 3 is a side view of the catheter accessory device of the present invention in an operative position on an inserted catheter and in an inoperative position in phantom.
Figure 4:
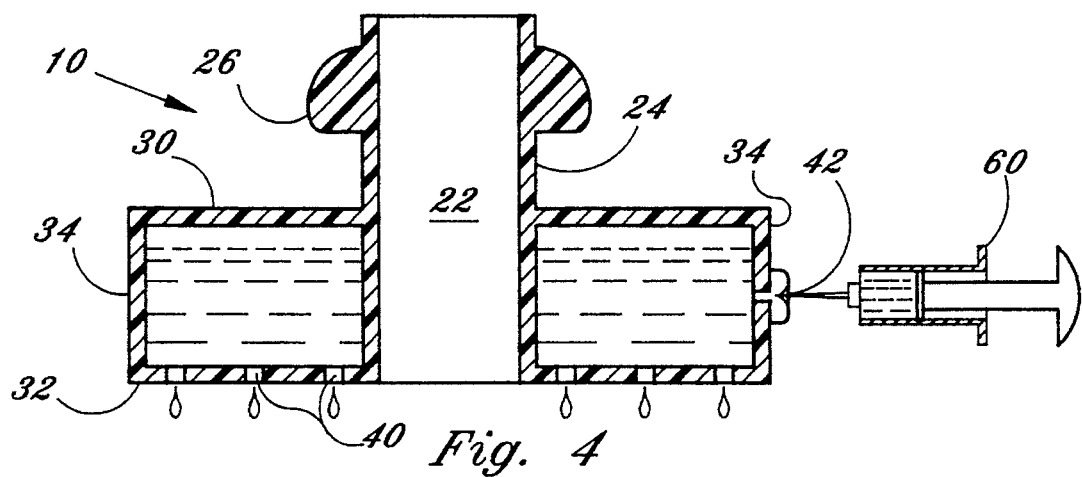
FIG. 4 is a side sectional view of the catheter accessory device of the present invention.
Figure 6:
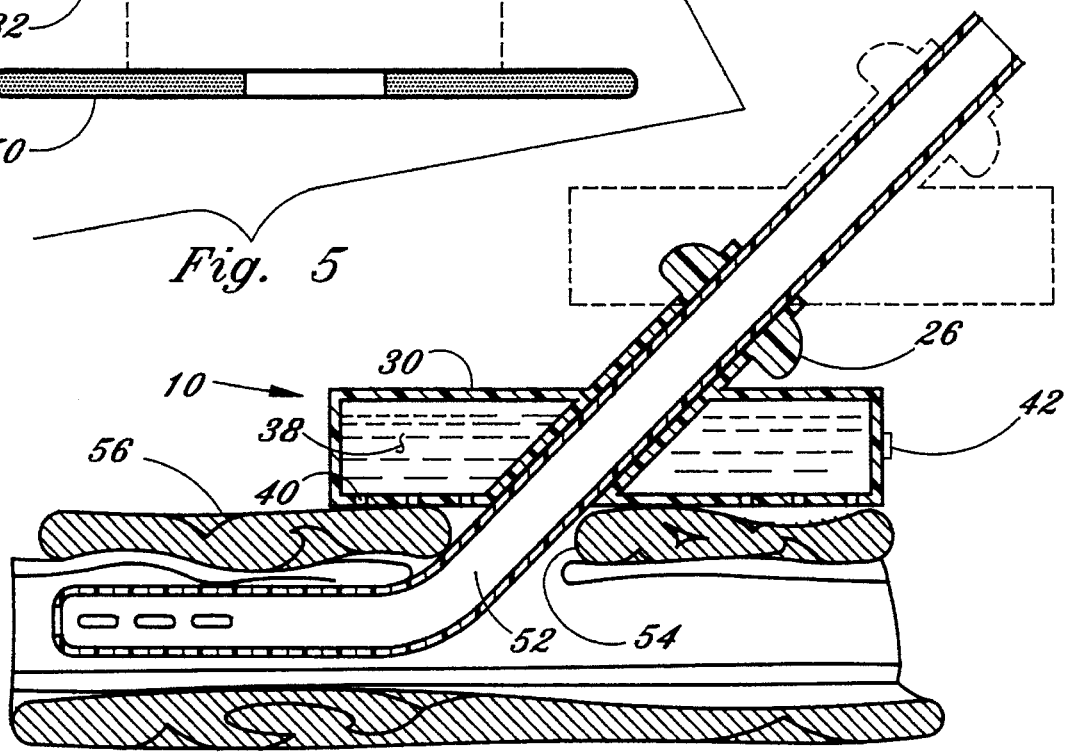
FIG. 6 is a sectional view of a second alternate embodiment of the catheter accessory device of the present invention.

As best depicted in FIGS. 3 and 6, there is shown alternate embodiments of the instant invention 10 installed on a catheter 52. Device body aperture 22 may exist in coaxial alignment with top and bottom surfaces 30 and 32 axes, as depicted in FIG. 3, or aperture 22 may exist acutely angled, in non-coaxial alignment, with top and bottom surfaces 30 and 32 axes, for conforming to the angle of catheter insertion, as best depicted in FIG. 6. As can best be seen in the embodiment depicted in FIG. 6, the angled body aperture 22 facilitates minimal catheter curvature for reducing the likelihood of internal catheter flow restriction and/or tissue damage.

Figure 7:
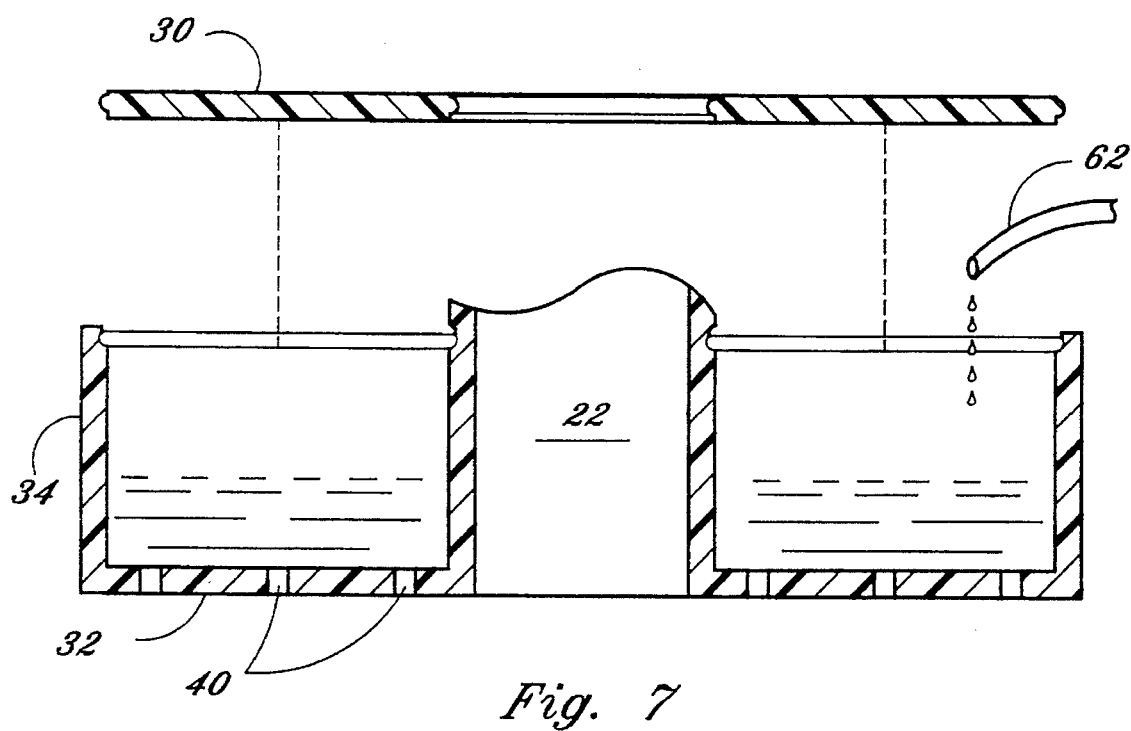
FIG. 7 is a sectional view of a third alternate embodiment of the catheter accessory device of the present invention having a removable top section to facilitate filling.
Figure 8:
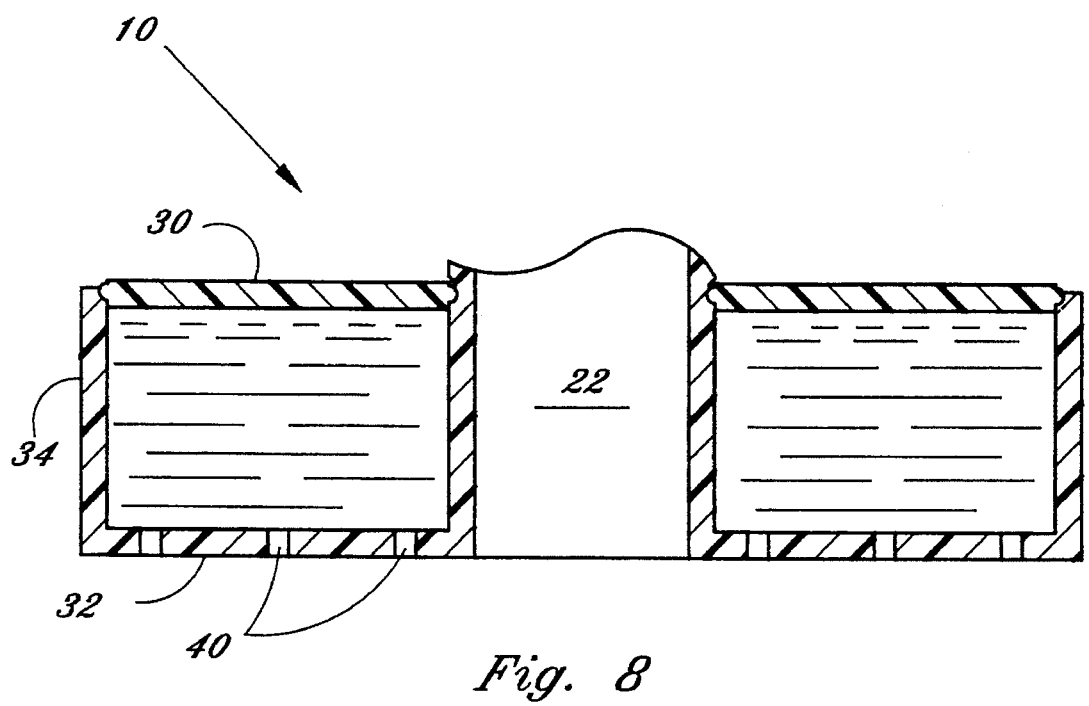
FIG. 8 is a sectional view of the third alternate embodiment shown in FIG. 7 but with the top separated.

In FIGS. 7 and 8 there is shown an alternate embodiment in sectional view wherein top surface 30 includes a removable top. In this embodiment, top surface 30 is shown in the attached position in FIG. 8, and removed, as for antiseptic filling purposes, in FIG. 7. Top surface 30 may also be hingedly connected. While a removable or hingedly connected top is disclosed, any antiseptic filling means is within the scope of the invention.

Figure 9:
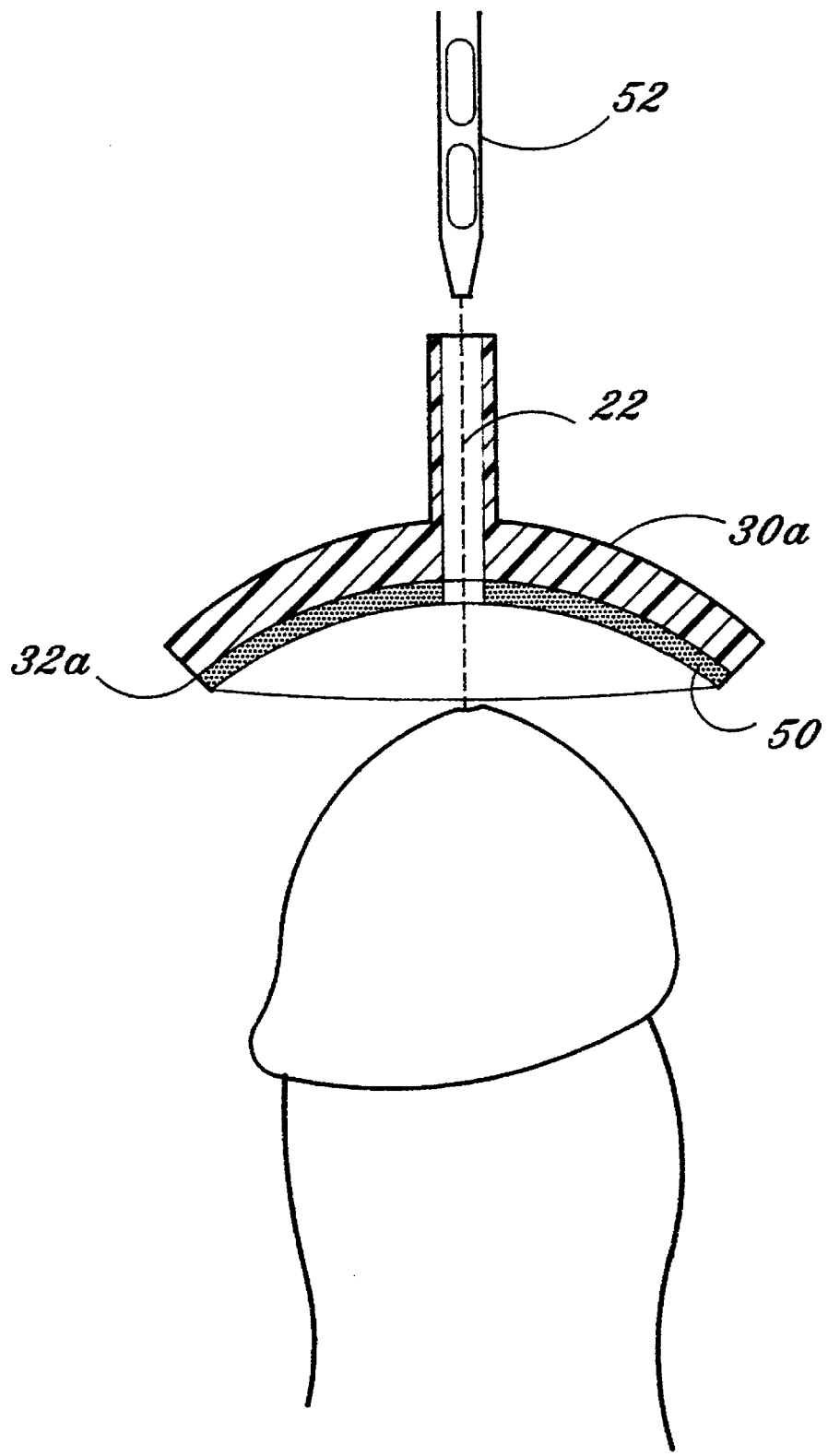
FIG. 9 is a sectional view of a fourth alternate embodiment for use with a urethral catheter.

In FIG. 9 there is depicted a urethral catheter embodiment for preventing urinary tract infections associated with catheterization. This embodiment contemplates a concave bottom surface 32a and a convex top surface 30a, for conforming to a male penis. As with the aforementioned embodiments, the embodiment depicted in FIG. 9 may incorporate an antiseptic impregnated pad 50, or an antiseptic reservoir and dispensing apertures (not shown). The invention naturally contemplates a different configuration for use with the female anatomy (not shown) that may be flat or of other suitable shape, rather than concave, and be of a suitable size.

As previously noted, each of the aforementioned embodiments may also comprise a substantially C-shaped body, in lieu of the donut shapes depicted, for allowing the device to be attached to, and removed from, an inserted catheter without requiring the removal of the catheter. The C-shaped embodiment is particularly desirable in situations where catheter removal is infrequent. It is contemplated that any peripheral gap in the C-shaped embodiment be minimized or eliminated such that antiseptic solution is dispensed around the entire catheterization site periphery.

To use the present invention, the device 10 is slidably attached to a catheter by insertion of a catheter end through body aperture 22 as seen in FIGS. 3 and 6, or clipped to the catheter (not shown). After attachment, the device 10 is positioned adjacent the catheterization site by sliding body 20 along the catheter until lower surface 32 contacts the tissue surrounding the site. Accordingly, antiseptic or antibiotic solution is dispersed on the tissue surrounding the catheterization site via apertures 40, or impregnated pad 50, thereby reducing the microbiological population surrounding the site and preventing infection.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A device for use with medical catheters for preventing, or reducing the incidence of, catheter-related infection originating at the site of catheter insertion into the patient's body comprising:

a body defining a centrally disposed aperture therethrough;

means associated with said body for dispensing antiseptic, wherein said means for dispensing antiseptic includes a reservoir, housed within said body and containing a supply of antiseptic, said body defining a plurality of openings communicating with said reservoir for dispensing said antiseptic proximal the catheter insertion site.

2. A device for use with medical catheters for reducing the incidence of catheter-related infection originating at the site of catheter insertion into the patient's body comprising:

a generally C-shaped body, said body defining a centrally disposed aperture therethrough;

said body housing a reservoir for containing a supply of antiseptic;

said body including means for dispensing antiseptic from said reservoir thereby preventing infection originating at the site;

means associated with said body for filling said reservoir with antiseptic.

3. A device for use with medical catheters according to claim 2, wherein said means for filling said reservoir comprises a self sealing fill port communicating with said reservoir, said fill port sized for accommodating a hypodermic needle inserted therethrough for filling said reservoir using a syringe.

4. A device for use with medical catheters according to claim 2, wherein said means for filling said reservoir comprises a self sealing fill port communicating with said reservoir, said fill port sized for accommodating a syringe hub inserted therein for filling said reservoir using a syringe.

5. A device for use with medical catheters according to claim 2, further including means for grasping said device, said means for grasping comprising at least one protruding tab attached to said body.

6. A device for use with medical catheters according to claim 5, wherein said means for grasping further functions as an anchoring structure for securing said device at a desired position adjacent the catheter insertion site using surgical sutures.

7. A device for use with medical catheters for reducing the incidence of catheter-related infection originating at the site of catheter insertion into the patient's body comprising:

a disk shaped body, said body defining a centrally disposed aperture therethrough;

said body housing a reservoir for containing a supply of antiseptic solution;

said body having a bottom surface, said bottom surface incorporating a plurality of antiseptic dispensing openings in communication with said reservoir such that antiseptic is dispensed proximal the catheter insertion site through said openings.

8. A device for use with medical catheters according to claim 7, wherein said body bottom surface is substantially planar.

9. A device for use with medical catheters according to claim 7, wherein said body bottom surface is concave.

10. A device for use with medical catheters according to claim 7, wherein said body aperture is acutely angled.

11. A device for use with medical catheters according to claim 7, wherein said body further includes a removable portion, whereby removal of said removable portion provides access for filling said reservoir with antiseptic.

* * * * *